United States Patent
Yoon et al.

(10) Patent No.: US 8,435,250 B2
(45) Date of Patent: May 7, 2013

(54) MICRO MANIPULATOR FOR ELECTRODE MOVEMENT IN NEURAL SIGNAL RECORDING

(75) Inventors: Eui Sung Yoon, Seoul (KR); Sung Wook Yang, Gimpo-si (KR); Jin Seok Kim, Seoul (KR); Duk Moon Rho, Seoul (KR); Ki Tae Park, Incheon (KR); Se Min Lee, Seoul (KR); Jei Won Cho, Uiwang-si (KR); Hee Sup Shin, Uiwang-si (KR)

(73) Assignee: Korea Institute of Science and Technology, Seoul (KR)

( * ) Notice: Subject to any disclaimer, the term of this patent is extended or adjusted under 35 U.S.C. 154(b) by 551 days.

(21) Appl. No.: 12/541,558

(22) Filed: Aug. 14, 2009

(65) Prior Publication Data

US 2010/0168759 A1 Jul. 1, 2010

(30) Foreign Application Priority Data

Dec. 29, 2008 (KR) .................. 10-2008-0135977

(51) Int. Cl.
*A61B 19/00* (2006.01)

(52) U.S. Cl.
USPC ...... 606/129; 606/130; 310/323.06; 310/328; 607/116; 607/139; 607/149; 314/27; 314/39

(58) Field of Classification Search .................. None
See application file for complete search history.

(56) References Cited

U.S. PATENT DOCUMENTS

| | | | | |
|---|---|---|---|---|
| 4,139,948 A | * | 2/1979 | Tsuchiya et al. | 359/391 |
| 5,237,238 A | * | 8/1993 | Berghaus et al. | 310/328 |
| 5,776,114 A | * | 7/1998 | Frantzen et al. | 604/531 |
| 6,140,750 A | * | 10/2000 | Ueyama | 310/369 |
| 7,141,914 B2 | * | 11/2006 | Kallio et al. | 310/323.17 |
| 2001/0020455 A1 | * | 9/2001 | Schifferl | 123/90.11 |
| 2004/0122446 A1 | * | 6/2004 | Solar | 606/129 |
| 2005/0197556 A1 | * | 9/2005 | Stoler | 600/383 |
| 2007/0296310 A1 | * | 12/2007 | Kim et al. | 310/338 |

OTHER PUBLICATIONS

Philips, Magnetoresistive Sensors for Magnetic Field Measurement, Sep. 6, 2000.*
Philips, Magnetoresistive Sensors for Magnetic Field Measurement, Semiconductors, Sep. 6, 2000.*
Sungwook Yang, et al., "Piezo motor based Microdrive for Neural Signal Recording", paper filed at EMBC 2008 conference, Aug. 20-Aug. 24, 2008.
Sungwook Yang, et al., "Piezo Motor based Microdrive for Neural Signal Recording", poster presentation at Neuroscience 2008 conference, Nov. 15-Nov. 19, 2008.

* cited by examiner

*Primary Examiner* — Katherine Dowe
*Assistant Examiner* — Sidharth Kapoor
(74) *Attorney, Agent, or Firm* — Ohlandt, Greeley, Ruggiero & Perle, L.L.P.

(57) ABSTRACT

This disclosure relates to a micro manipulator having a simple structure and having high possibility of recording a biological signal of a neuron at a desired position by improving positioning resolution of an electrode disposed adjacent to a subject's brain neuron or an electrode holder attached with the electrode. The micro manipulator according to the disclosure includes: a motor which includes a shaft and a vibration portion; a mobile which is connected to the shaft so as to be movable along the shaft; and a frame which supports the motor, wherein an electrode is connected to the mobile in a direction parallel to a longitudinal direction of the shaft, and wherein when the mobile moves linearly in accordance with a vibration of the shaft due to the vibration portion, the electrode moves linearly.

12 Claims, 16 Drawing Sheets

MICRO MANIPULATOR FOR ELECTRODE MOVEMENT IN NEURAL SIGNAL RECORDING

CROSS-REFERENCE TO RELATED APPLICATIONS

This application claims priority to Korean Patent Application No. 10-2008-0135977, filed on Dec. 29, 2008, and all the benefits accruing therefrom under 35 U.S.C. §119, the contents of which in its entirety are herein incorporated by reference.

BACKGROUND

1. Field

This disclosure relates to a micro manipulator for an electrode movement, and more particularly, to a micro manipulator capable of improving positioning resolution and positioning ability of an electrode disposed adjacent to a subject's neuron or an electrode holder attached with the electrode with a simple structure.

2. Description of the Related Art

A living organism has numerous neurons, and the neurons are used as information transmitting means. A method of transmitting information between neurons is understood as an electrical signal transmitting and receiving process. That is, the neurons transmit information to other neurons via an electrical signal. This means that the neurons are sensitive to the external electrical stimulus.

Electrophysiology is the study of relationships between the living organism and the electricity. In other words, electrophysiology is the study examining an influence of the electricity on the living body and an electrical phenomenon occurring in the living body. Electrophysiology has been rapidly developed with the development of electronic engineering and the technology of inserting an electrode into a cell.

It is known that there exist about $10^{11}$ neurons in the human brain. The neurons in the brain determine the function of the brain, and are classified variously according to their functions. Accordingly, in order to understand the function of the brain, it is necessary to analyze the role and the operation of the brain neurons. For the purpose of analyzing the function of the brain neurons, there is proposed a method of analyzing the electric characteristic of the brain neurons in accordance with the external stimulus and the reaction of the living body in accordance with the electrical stimulus for specific brain neurons. However, since the electrical stimulation method cannot be performed on the human, experiments are carried out on animals.

FIG. 1 is a schematic conceptual diagram showing an experiment device which is used for an experiment for examining a relationship between the brain neuron and electricity. As shown in FIG. 1, generally, a small animal such as a mouse is used as a subject for the experiment for examining the relationship between the brain neuron and electricity. In order to locate an electrode, which detects an electrical signal of the subject's brain neuron and applies an electrical signal to the brain neuron, so as to be adjacent to the brain neuron, a micro manipulator 1 is used. The micro manipulator 1 is connected to an external signal processing device 2. The external signal processing device 2 includes a controller which controls an operation of the micro manipulator 1, a signal processing portion which converts an electrical signal generated from the electrode into a digital signal and analyzes the result, or the like.

Since the brain is the most sensitive organ, a process of applying the electrical stimulus to the brain neuron or extracting the electrical signal therefrom has to be performed very carefully. Accordingly, in the above-described brain neuron electrical signal analyzing device, the micro manipulator for performing an operation of moving the electrode to be adjacent to the brain neuron plays a very important role from the viewpoint of obtaining accurate experimental data and of protecting the living body.

In the past, in order to perform the operation of moving the electrode to be adjacent to the brain neuron, a manual micro manipulator or a micro manipulator using a small motor was used.

In the manual micro manipulator, an operator needs to restrain the animal used in the experiment and to operate a moving device. Accordingly, the experiment is difficult, and the positioning ability of the electrode deteriorates due to the manual operation. In addition, a problem arises in that the electrode may be detached from the neuron to be recorded due to the subject animal's resistance.

In order to solve the above-described problems, a micro manipulator using an existing small motor is developed. However, since the known micro manipulator includes a gear portion transmitting an operation of the motor, a moving device such as a screw used for the linear movement of the electrode, and the like, a problem arises in that a longitudinal length of the manipulator increases and a structure is complex. In addition, since an error occurs easily in a meshing operation between various mechanical components such as reduction gears and a screw, a problem arises in that the resolution of the micro manipulator for moving the electrode is not high and the control ability deteriorates due to the low resolution.

SUMMARY OF THE INVENTION

To solve the above-described known problems, this disclosure is directed to providing a micro manipulator having a simple structure and having excellent resolution and positioning ability in such a manner that a mobile moves linearly by using a motor including a shaft and a vibration portion, so as to move an electrode connected to the mobile.

In one aspect, there is provided a micro manipulator including: a motor which includes a shaft and a vibration portion; a mobile which is connected to the shaft so as to be movable along the shaft; and a frame which supports the motor, wherein an electrode is connected to the mobile in a direction parallel to a longitudinal direction of the shaft, and wherein when the mobile moves linearly in accordance with a vibration of the shaft due to the vibration portion, the electrode moves linearly.

The vibration portion may include a deforming plate which extends and contracts upon applying a power thereto and an elastic plate which is attached to the deforming plate. The shaft may be fixed to the deforming plate or the elastic plate and is formed in a direction perpendicular to the elastic plate.

The micro manipulator further includes an electrode holder which is fixed to the mobile and is formed in a direction parallel to the longitudinal direction of the shaft. The electrode may be mounted to the inside of the electrode holder so as to be connected to the mobile.

The electrode holder may be separable from the mobile.

The shaft may perforate the center of the frame.

The micro manipulator further includes a funnel-shaped guide member. The guide member may be coupled to the center of a lower end of the frame so that an end of the electrode extends along an axis of the shaft.

The micro manipulator further includes a position sensor which measures a displacement of the mobile.

The position sensor may include a permanent magnet and a magnetoresistive sensor. The permanent magnet may be fixed to the mobile.

The micro manipulator further includes a control signal transmitting device which receives a control signal generated by a controller so as to operate the motor.

The micro manipulator further includes a neural signal transmitting device which transmits a signal detected by the electrode to the outside.

The micro manipulator further includes a position signal transmitting device which transmits displacement information of the mobile measured by the position sensor to the outside.

The micro manipulator further includes an outer cover which supports the motor, the mobile and the frame therein in a fixed state.

The outer cover may include an upper cover and a lower cover. The upper cover may be separable from the lower cover.

The micro manipulator further includes a plate spring which is coupled to the mobile. The plate spring may be located at a connection portion between the shaft and the mobile so as to apply frictional force between the shaft and the mobile.

The micro manipulator according to the disclosure has a simple structure and may be formed with a small size. Accordingly, the micro manipulator is easily attachable to a small subject, and a motion of the subject with the micro manipulator attached thereto is not limited.

In addition, since the micro manipulator according to the disclosure has excellent resolution and positioning ability and is easily controlled, it is advantageous in that the micro manipulator is usable for a precise experiment.

BRIEF DESCRIPTION OF THE DRAWINGS

The above and other aspects, features and advantages of the disclosed exemplary embodiments will be more apparent from the following detailed description taken in conjunction with the accompanying drawings in which:

FIG. 9 is a graph showing a result of an experiment of driving the micro manipulator according to the embodiment in FIG. 7;

DETAILED DESCRIPTION

Figure 1:
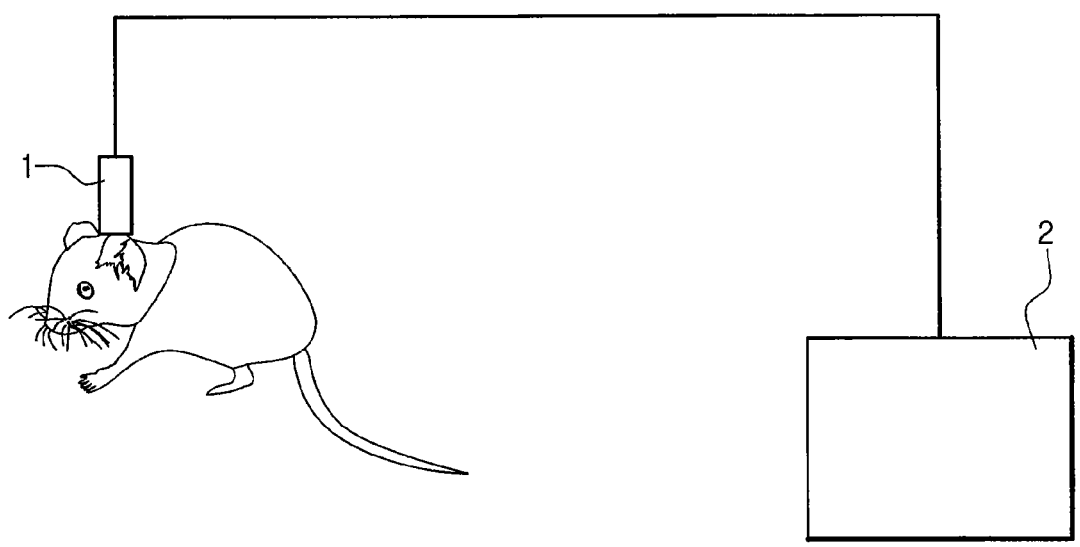
FIG. 1 is a schematic conceptual diagram showing an experiment device which is used for an experiment for examining a relationship between brain neurons and electricity.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

Hereinafter, exemplary embodiments of the disclosure will be described with reference to the accompanying drawings.

Figure 2:
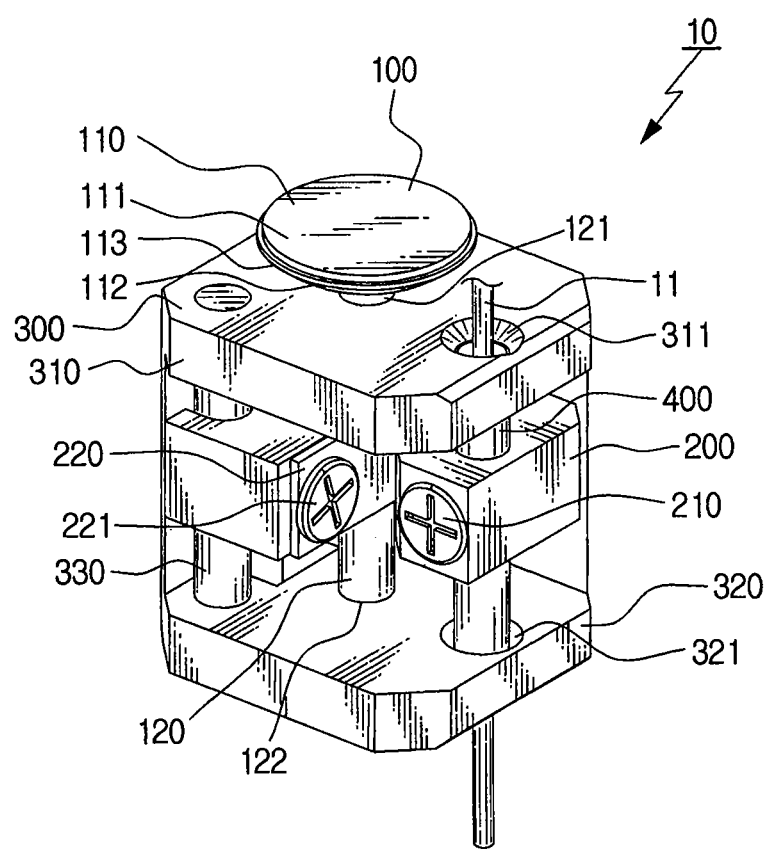
FIG. 2 is a perspective view showing a micro manipulator 10 according to an embodiment of the disclosure.
Figure 3:
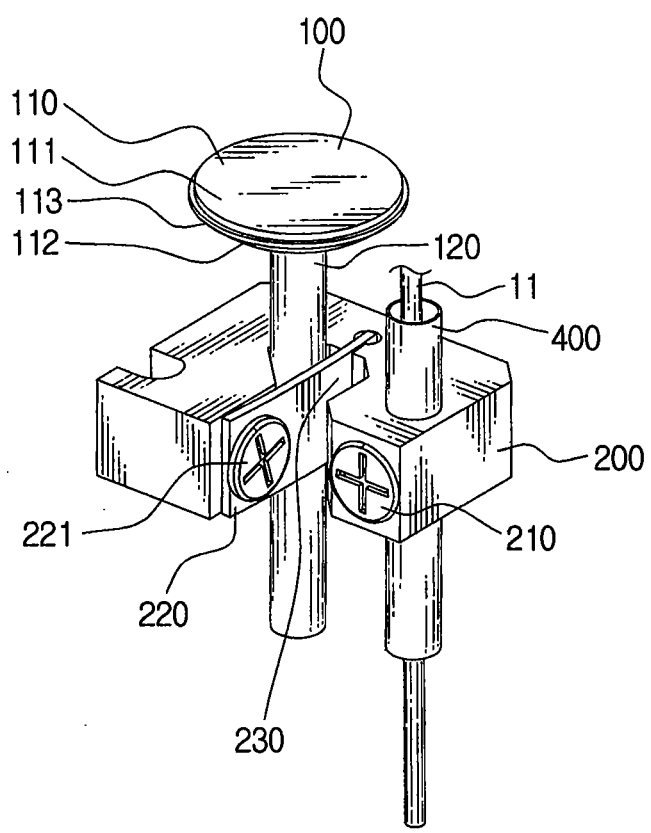
FIG. 3 is a partial perspective view showing the micro manipulator according to the embodiment in FIG. 2.

FIG. 2 is a perspective view showing a micro manipulator 10 according to an embodiment of the disclosure. FIG. 3 is a partial perspective view showing the micro manipulator according to the embodiment in FIG. 2.

As shown in FIG. 2, a micro manipulator 10 according to the embodiment includes a motor 100, a mobile 200, and a frame 300 which supports the motor 100. The motor 100 includes a vibration portion 110 which has plural thin plates 111, 112, and 113 combined with each other and a shaft 120 which is formed in a direction perpendicular to the vibration portion 110. As shown in FIG. 3, the shaft 120 is connected to the mobile 200. The mobile 200 is formed in a substantially U-shape and has a V-shaped groove 230 formed at the center thereof. After the shaft 120 is located inside of the V-shaped groove 230 of the mobile 200, the shaft 120 is coupled to a plate spring 220 through a bolt 221.

By means of the above-described coupling operation, the mobile 200 is connected to the shaft 120 so as to be movable linearly along the shaft 120 in the vertical direction. At this time, the plate spring 220 generates a frictional force between the mobile 200 and the shaft 120 by an elastic restoring force. Accordingly, in order to move the mobile 200 along the shaft 120, a force which is equal to or larger than the elastic restoring force of the plate spring 220 has to be applied.

An electrode 11 which is inserted into a subject for detection of a neural signal is connected to the mobile 200 in a direction parallel to the shaft 120. The micro manipulator 10 according to the embodiment is provided with a hollow electrode holder 400 used to connect the electrode 11 to the mobile 200.

As shown in FIG. 3, the electrode holder 400 is fixed to the mobile 200 in a direction parallel to the shaft 120, and the electrode 11 is fixed to the electrode holder 400 so as to extend through an inner hole thereof. By means of the above-described coupling operation, when the mobile 200 moves in the vertical direction, the electrode holder 400 moves, and the electrode 11 fixed to the electrode holder 400 moves in the vertical direction. That is, the electrode 11 moves linearly in accordance with the linear movement of the mobile 200.

The electrode holder 400 is separable from the mobile 200. As shown in FIGS. 2 and 3, the electrode holder 400 is fixed to the mobile 200 through a bolt 210. Accordingly, it is possible to separate the electrode holder 400 from the mobile 200 by removing the bolt 210. That is, after the experiment, the electrode holder 400 and the electrode 11 may be separated from the mobile 200 for the purpose of replacement with a new electrode holder 400 and a new electrode 11. Accordingly, it is possible to recycle the micro manipulator 10.

The motor 100 is supported by the frame 300. As shown in FIG. 2, the shaft 120 of the motor 100 is connected to the frame 300 by passing through the centers of upper and lower plates 310 and 320 thereof. When the motor 100 is connected to the frame 300 by passing through the center thereof, since the center of mass of the micro manipulator 10 is near the center thereof, the structure becomes stabilized. In addition, the transverse size of the micro manipulator 10 decreases. Connection portions 121 and 122 between the shaft 120 and the upper and lower plates 310 and 320 are fixed by using an epoxy or the like. That is, the shaft 120 is not rigidly coupled to the frame 300, but is coupled to the frame 300 with a strength so that the shaft 120 is not separated from the frame 300. Accordingly, the shaft 120 is fixed to the frame 300 so as to permit a minute vibration thereof in the vertical direction.

As shown in FIG. 2, the mobile 200 is located in a space formed between the upper and lower plates 310 and 320 of the frame 300. Since perforation holes 311 and 321 are formed in the upper and lower plates 310 and 320 of the frame 300, the electrode holder 400 and the electrode 11 are movable in the vertical direction without any disturbance. In addition, a fixed shaft 330 is provided on one side of the space, formed between the upper and lower plates 310 and 320 of the frame 300, so as to prevent the mobile 200 from moving due to the vibration of the shaft 120.

According to the embodiment, the mobile 200 moves linearly in accordance with the vibration of the shaft 120, and the electrode holder 400 moves linearly in accordance with the linear movement of the mobile 200, thereby moving the electrode 11 connected to the electrode holder 400 linearly.

For the purpose of the vibration of the shaft 120, in the embodiment, a motor is used which includes the vibration portion 110 having deforming plates 111 and 112 extending or contracting upon applying a power thereto and an elastic plate 113 attached to the deforming plates 111 and 112, and the shaft 120 which is fixed to the deforming plate 112 in a direction perpendicular thereto. Such a motor is called a piezo motor. The deforming plates 111 and 112 are formed with a piezoelectric material or an electrostrictive material which causes mechanical deformation such as extension or contraction upon application of a power thereto. Single-crystalline ceramics, polycrystalline ceramics, polymers, or the like are generally used as the piezoelectric material or electrostrictive material for forming the deforming plates 111 and 112, but the disclosure is not limited thereto. The elastic plate 113 is an elastic body having elasticity.

In FIGS. 2 and 3, the piezo motor is shown in which the deforming plates 111 and 112 are respectively attached to the upper and lower ends of the elastic plate 113, but the disclosure is not limited thereto.

FIGS. 4A to 4F are conceptual diagrams showing an operation principle of the micro manipulator 10 according to the embodiment of the disclosure. As shown in FIGS. 4A to 4F, the motor 100 of the micro manipulator 10 includes the deforming plate 111 which is a piezoelectric material, the elastic plate 113 which is coupled to the deforming plate 111, and the shaft 120 which is fixed to the elastic plate 113 in a direction perpendicular thereto.

Figure 4A:
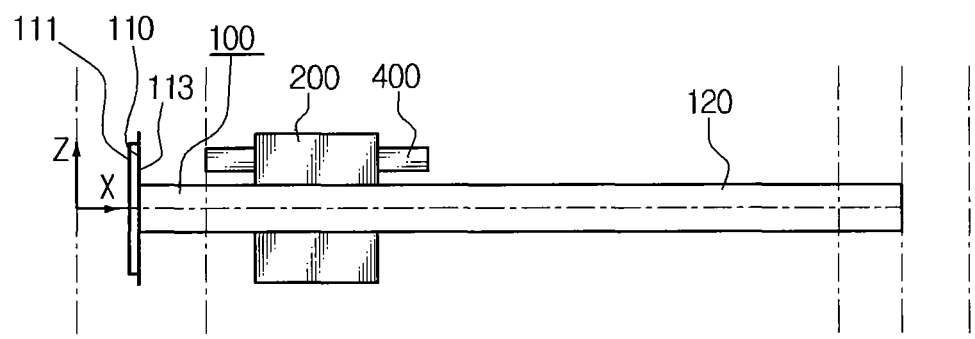
FIGS. 4A to 4F are conceptual diagrams showing an operation principle of the micro manipulator 10 according to the embodiment of the disclosure.
Figure 4B:
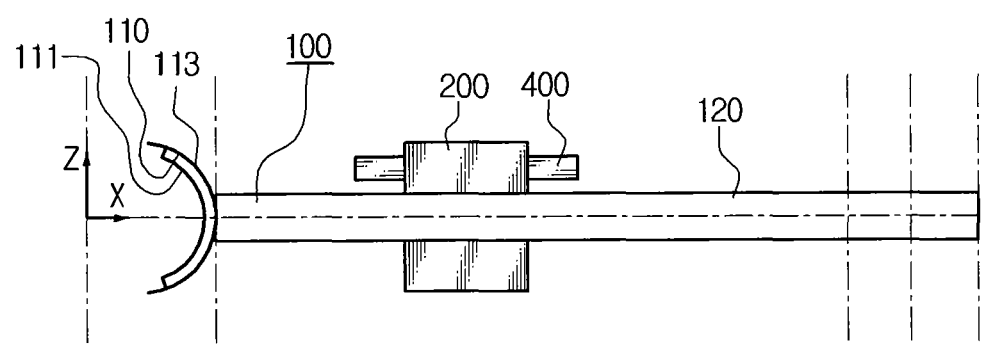

FIG. 4A shows a state where the shaft 120 and the mobile 200 are located at an initial position. When an appropriate power is applied to the deforming plate 111 in the state of FIG. 4A, as shown in FIG. 4B, the deforming plate 111 contracts in the z direction. When the deforming plate 111 contracts in the z direction, the deforming plate 111 extends in the x direction due to the Poisson's ratio. The deforming plate 111 and the elastic plate 113 are fixed to each other. Accordingly, when the deforming plate 111 is mechanically displaced as described above, the elastic plate 113 is curved in the +x direction, and hence the vibration portion 110 is curved in the +x direction. When the vibration portion 110 is mechanically displaced to be curved, the shaft 120 moves rightward due to the displacement. Since an elastic body (not shown) such as a plate spring applies a frictional force between the shaft 120 and the mobile 200, when the shaft 120 moves rightward, the mobile 200 also moves rightward as shown in FIG. 4B. Accordingly, the electrode holder 400 fixed to the mobile 200 also moves rightward. Although it is not shown in FIG. 4B, the electrode is connected to the electrode holder 400, and hence the electrode advances in accordance with the above-described movement so as to be inserted into the subject by a predetermined depth.

Figure 4C:
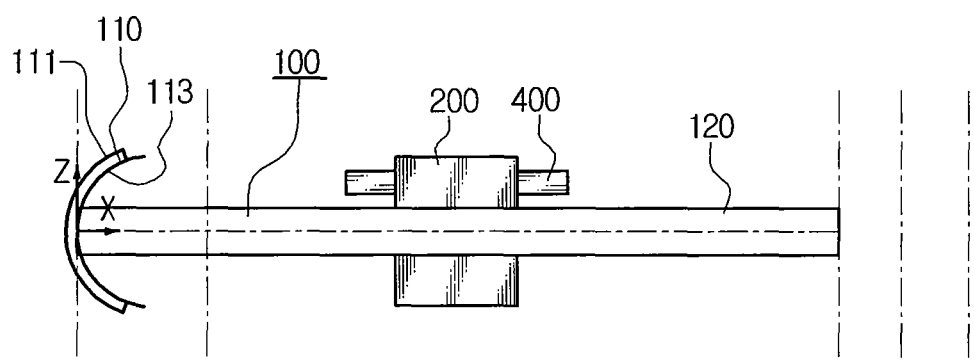
Figure 4D:
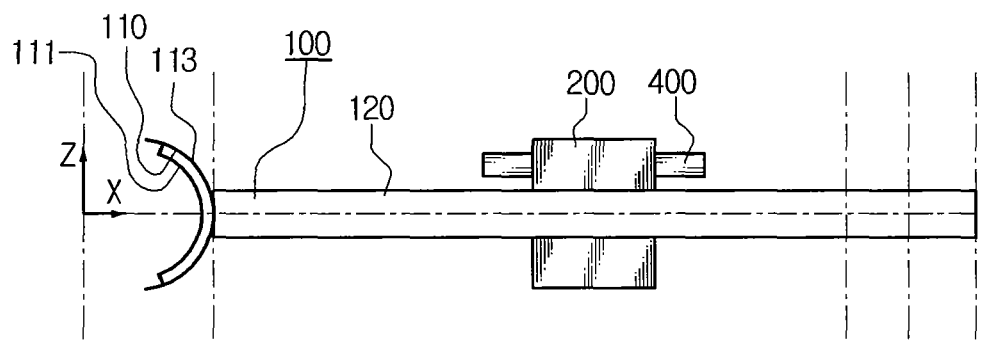
Figure 4E:
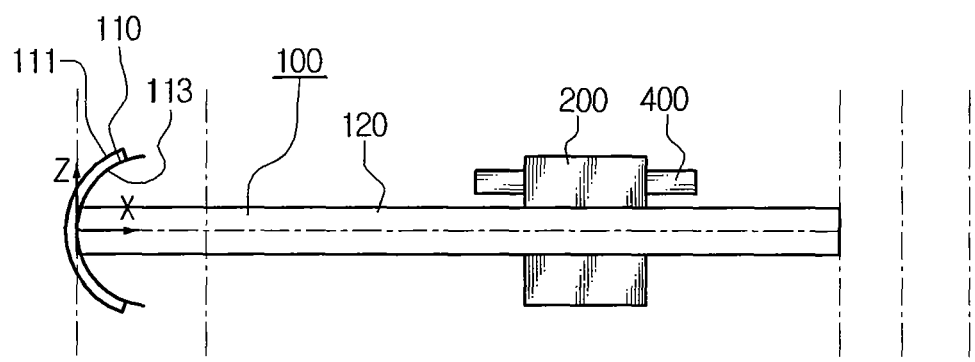
Figure 4F:
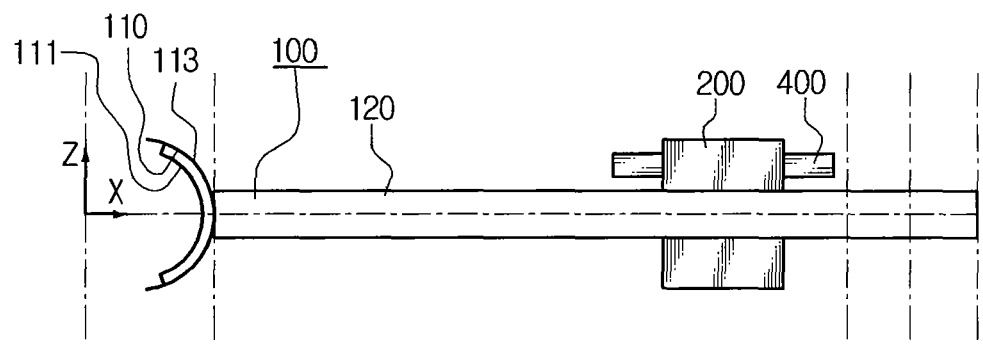

At this time, as shown in FIG. 4C, when the supply of power to the vibration portion 110 is cut off, the vibration portion 110 instantly returns to its original position by the restoring force of the elastic plate 113, and is curved in the −x direction by the movement distance in the +x direction due to the inertia force. Accordingly, as shown in FIG. 4C, the shaft 120 instantly moves in the −x direction. At this time, since the mobile 200 has a weight, the mobile 200 is maintained at its current position without moving together with the shaft 120 due to the inertia.

When a power is applied to the deforming plate 111 again, as shown in FIG. 4 D, the vibration portion 110 is curved again in the +x direction so that the mobile 200 moves in the +x direction. At this time, the supply of power is cut off again, as shown in FIG. 4E and then a power is applied to the deforming plate 111 again, as shown in FIG. 4F, the mobile 200 moves gradually. As will be easily understood by the person skilled in the art, when an appropriate power is applied to the deforming plate 111, the deforming plate 111 is vibrated in a direction opposite to that in FIGS. 4B, 4D and 4F so that the mobile 200 moves in the −x direction. More specially, when an appropriate power is applied to the deforming plate 111 in the state of FIG. 4A, the deforming plate 111 extends in the z direction. The deforming plate 111 and the elastic plate 113 are fixed to each other. Accordingly, when the deforming plate 111 is mechanically displaced as described above, the elastic plate 113 is curved in the −x direction, and hence the vibration portion 110 is curved in the −x direction. When the vibration portion 110 is mechanically displaced to be curved, the shaft 120 moves leftward together with the mobile 200 since an elastic body (not shown) such as a plate spring applies a frictional force between the shaft 120 and the mobile 200. Accordingly, the electrode holder 400 fixed to the mobile 200 also moves leftward. At this time, when the supply of power to the vibration portion 110 is cut off, the vibration portion 110 instantly returns to its original position by the restoring force of the elastic plate 113, and is curved in the +x direction by the movement distance in the −x direction due to the inertia force. Accordingly, the shaft 120 instantly moves in the +x direction. At this time, since the mobile 200 has a weight, the mobile 200 is maintained at its current position without moving together with the shaft 120 due to the inertia. When a power is applied to the deforming plate 111 again, the vibration portion 110 is curved again in the −x direction so that the mobile 200 moves in the −x direction. At this time, the supply of power is cut off again and then a power is applied to the deforming plate 111 again, the mobile 200 moves gradually is in the −x direction.

According to the embodiment, by means of the above-described principle, a power in the form of a periodical pulse wave is applied to the deforming plate 111 so as to move the vibration portion 110, and hence the shaft 120 connected thereto is vibrated. The mobile 200 moves linearly by the vibration of the shaft 120, and the electrode holder 400 connected to the mobile 200 moves linearly, thereby allowing the electrode to move close to or away from the subject's neuron.

In the embodiment, the piezo motor is used to move the mobile 200 linearly so that the electrode moves linearly, but the disclosure is not limited thereto. That is, the disclosure may adopt any configuration in which the shaft is periodically vibrated and the mobile moves linearly by the law of inertia.

In addition, in the above description, a power is applied to only to the deforming plate 111, but the disclosure is not limited thereto. For example, a power may be applied to both the deforming plate 111 and the elastic plate 113 so that the vibration portion 110 is controlled to vibrate periodically. It should be understood that the power application characteristic is variously modified in accordance with a specification such as the movement distance of the desired electrode and the elasticity of the elastic body which is located between the shaft 120 and mobile 200 so as to apply the frictional force thereto.

In the micro manipulator 10 according to the embodiment, it is possible to move the electrode linearly with a simple structure including the motor 100 and the mobile 200. Accordingly, since the structure is small in size and simple compared with the known technology, the micro manipulator 10 may be easily attached to a small animal such as a mouse and the motion of the animal with the micro manipulator 10 attached thereto is not limited.

In addition, the structure of driving means such as the piezo motor based on the law of inertia and vibration is simple compared with known other driving means. Further, since the piezo motor has high resolution, the positional precision and the positioning ability thereof are excellent. Accordingly, the micro manipulator 10 using the piezo motor is able to exhibit the extremely high resolution and positioning ability. According to actual measurements, the micro manipulator 10 using the piezo motor has a nanometer scale resolution of approximately 64 nm.

In order to precisely and accurately detect a signal generated from neurons of the small brain, the electrode used to detect a neural signal needs to be moved minutely. However, in a known manual micro manipulator or a known micro manipulator using a small motor, the electrode is moved using complex constituents such as a screw. Accordingly, the resolution and the positioning ability of the known micro manipulator are considerably lower than those of the same-sized micro manipulator 10 according to the disclosure. That is, in the known manual micro manipulator or the known micro manipulator using a small motor, in order to realize the nanometer resolution, the structure has to be large and complex due to the limitation of the constituents.

In contrast, since the micro manipulator 10 according to the disclosure has the high resolution and the simple structure as described above, the micro manipulator 10 may be appropriately used for the cases in which the micro manipulator used to detect the brain signal needs to be small in size and light in weight and the position of the electrode needs to be controlled precisely.

Figure 5:
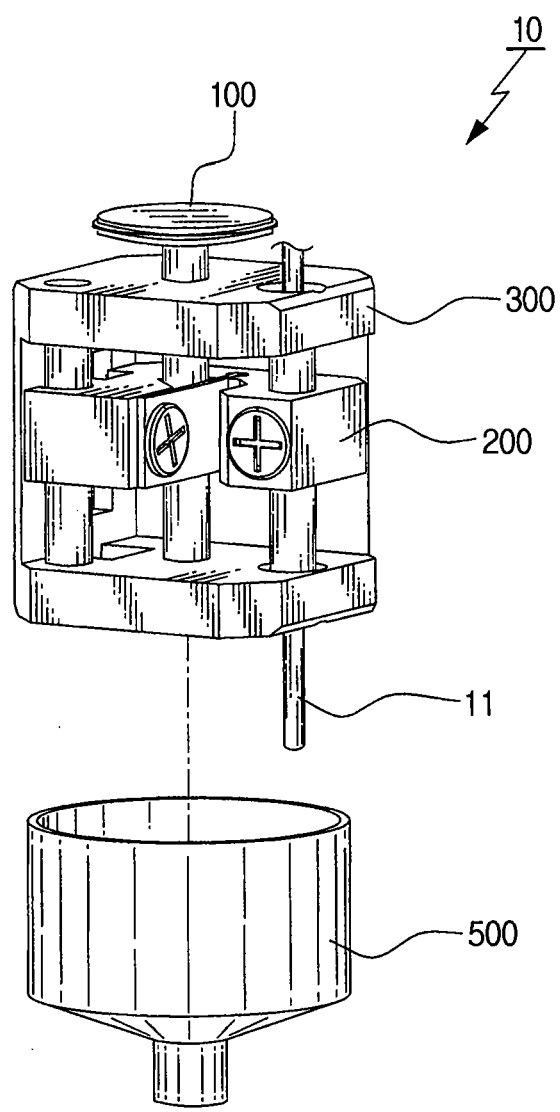
FIG. 5 is a perspective view showing a separated state of the micro manipulator 10 according to another embodiment of the disclosure.
Figure 6:
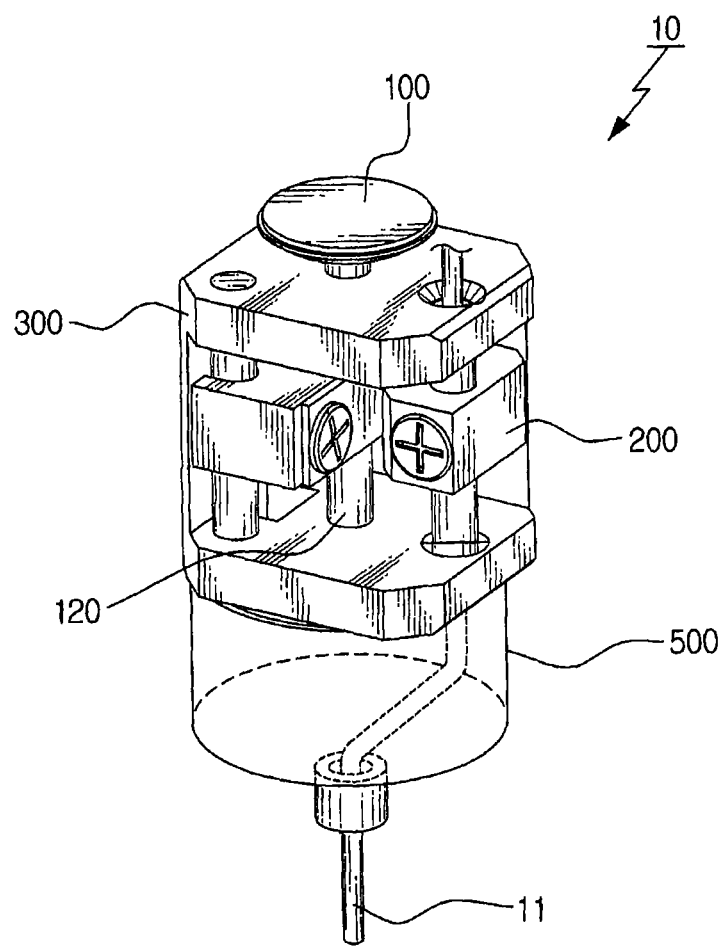
FIG. 6 is a perspective view showing a combined state of the micro manipulator 10 according to the embodiment in FIG. 5.

FIG. 5 is a perspective view showing a separated state of the micro manipulator 10 according to another embodiment of the disclosure. FIG. 6 is a perspective view showing a combined state of the micro manipulator 10 according to the embodiment in FIG. 5.

As shown in FIG. 5, since the motor 100 is coupled to the center of the frame 300, the electrode 11 is located at a position away from the center of the frame 300. When the electrode 11 is located at a position away from the center of the frame 300, since a distance between the center of the frame 300 and the electrode 11 needs to be considered when attaching the micro manipulator 10 to the subject so as to insert the electrode into a predetermined position, the installation of the micro manipulator 10 becomes complex.

Thus, according to the embodiment, a funnel-shaped guide member 500 is further provided. As shown in FIG. 6, the guide member 500 is coupled to the center of the lower end of the frame 300. The electrode 11 extends through the perforation hole formed in the lower end of the guide member 500 so as to be exposed to the outside. An end portion of the electrode 11 is located at the axis of the shaft 120, that is, the central axis of the frame 300 by the guide member 500. Accordingly, since the center of the frame 300 may be used as a reference when installing the micro manipulator 10, it is possible to easily install the micro manipulator 10 in the subject.

Figure 7:
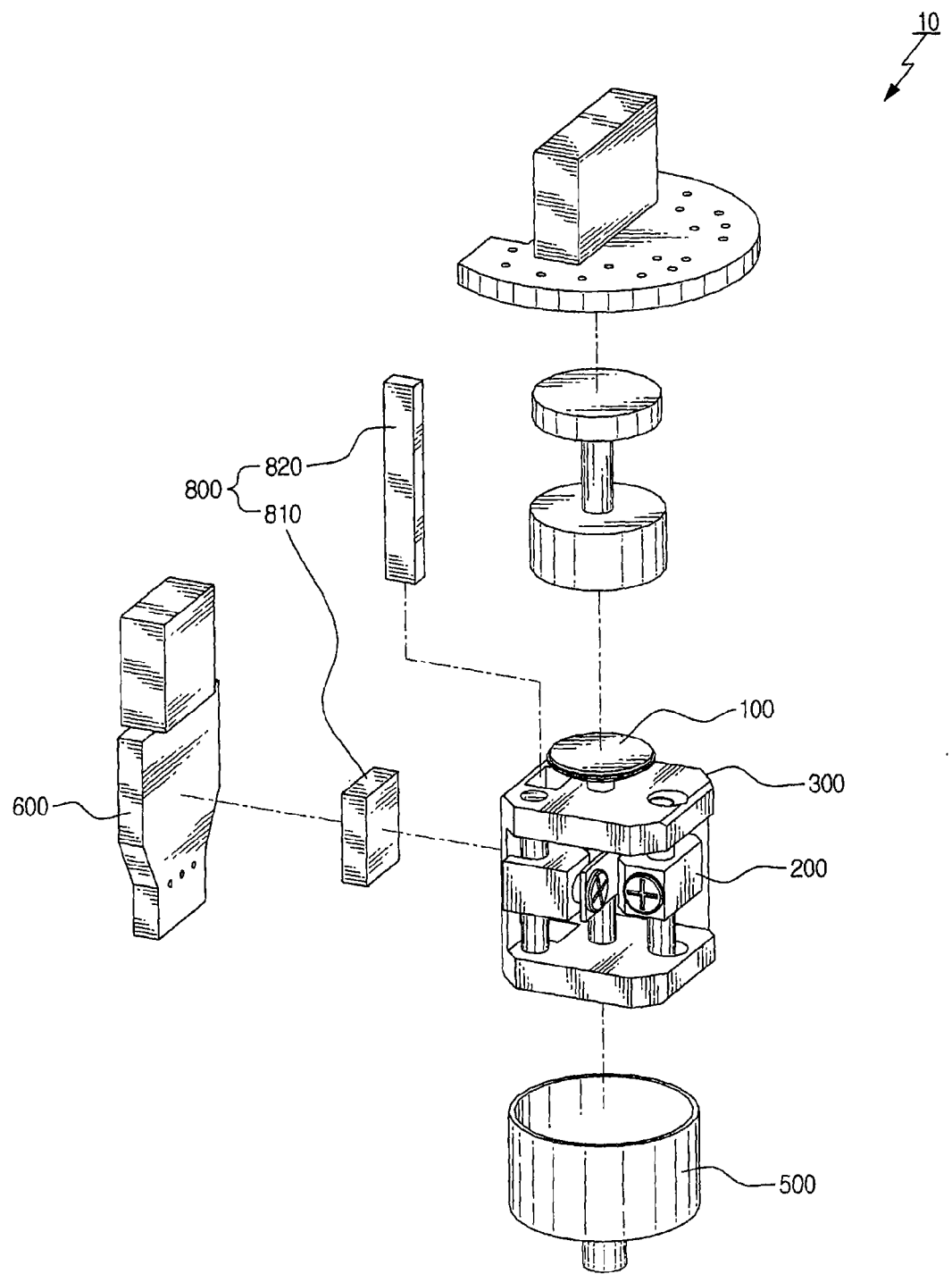
FIG. 7 is a perspective view showing a separated state of the micro manipulator 10 according to still another embodiment of the disclosure.
Figure 8:
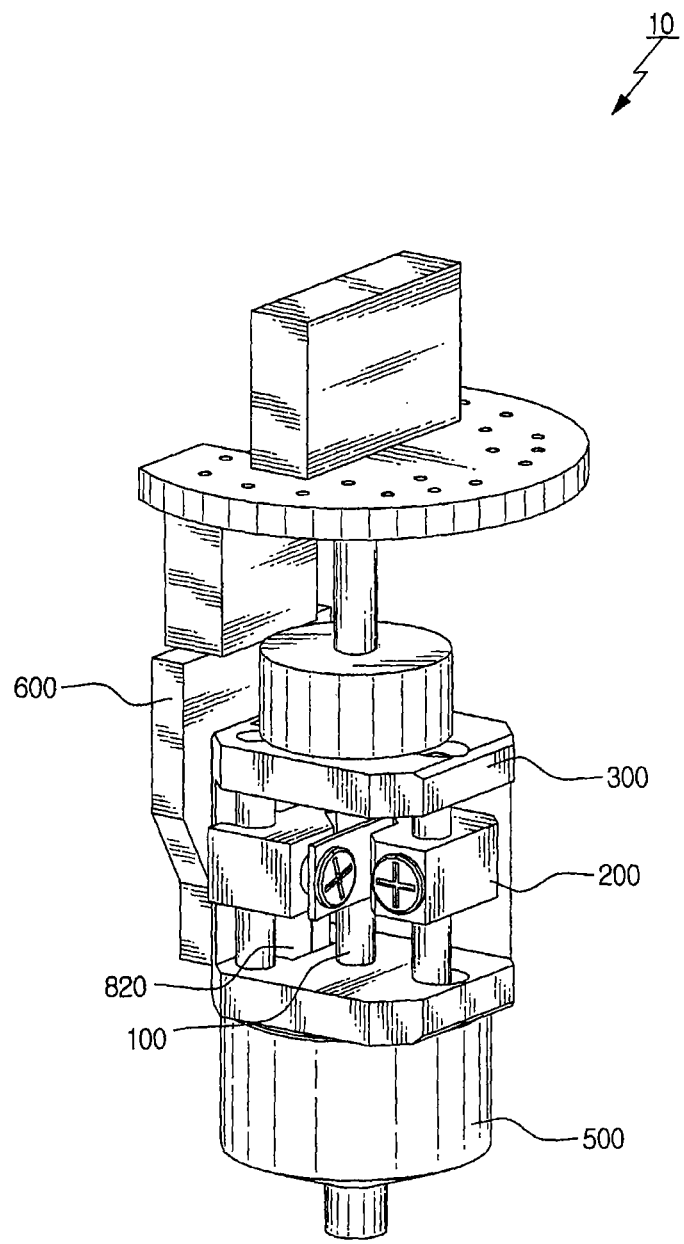
FIG. 8 is a perspective view showing a combined state of the micro manipulator 10 according to the embodiment in FIG. 7.

FIG. 7 is a perspective view showing a separated state of the micro manipulator 10 according to still another embodiment of the disclosure. FIG. 8 is a perspective view showing a combined state of the micro manipulator 10 according to the embodiment in FIG. 7.

As shown in FIG. 7, the micro manipulator 10 according to the embodiment includes a position sensor 800 including a permanent magnet 820 and a magnetoresistive sensor (MR sensor) 810. The position sensor 800 measures the position and the displacement of the mobile 200.

The permanent magnet 820 is fixed to the mobile 200 so as to move in a reciprocating manner together with the mobile 200. The magnetoresistive sensor 810 measures magnetism emitted from the permanent magnet 820 so as to measure and monitor the position of the permanent magnet 820 in real time, thereby obtaining position information of the mobile 200. When the current position of the mobile 200 is detected, it is possible to measure the current position of the electrode on the basis of the current position of the mobile 200.

The micro manipulator 10 according to the embodiment further includes a signal transmitting device 600. The signal transmitting device 600 according to the embodiment serves as a position signal transmitting device which transmits the position information of the mobile 200 measured by the magnetoresistive sensor 810 to an external controller and serves as a control signal transmitting device which transmits a motor control signal generated by the external controller so as to drive the motor 100.

The position information signal of the mobile 200 measured by the magnetoresistive sensor 810 is transmitted to the signal transmitting device 600 so as to be transmitted to the external controller, and the external controller combines the position information signal of the mobile 200 with the control signal for driving the motor 100. The motor control signal combined as described above is transmitted to the motor 100 via the signal transmitting device 600. The combined control signal is a signal including the accurate position information of the mobile 200. Accordingly, it is possible to drive the motor 100 so that the displacement of the mobile 200 is controlled to be always constant and to control the mobile 200 so that the electrode for detecting the neural signal is accurately located at a desired position.

Since the motor 100 of the micro manipulator 10 according to the embodiment moves the electrode by moving the mobile 200 through the vibration of the shaft 120, the displacement of the electrode is not linear depending on the increment of the number of input pulses due to internal or external loading. When the position information of the mobile 200 measured by the position sensor 800 as described above is fed back again to the external controller for controlling the motor 100, it is possible to control the mobile 200 to move linearly. Since there is a linear relationship between the movement of the electrode and the movement of the mobile 200, it is possible to control the movement of the electrode by controlling the movement of the mobile 200.

FIG. 9 is a graph showing a result of an experiment of driving the micro manipulator according to the embodiment in FIG. 7. In the graph, the x axis indicates the number of input steps, and the y axis indicates the actual displacement of the mobile 200. The motor 100 used in the experiment was a piezo motor having a driving frequency of 80 to 130 Hz, a driving voltage of 12 to 30 V, and a current of 5 to 20 mA.

A laser vibrometer was used to measure the displacement of the mobile 200, and the step input signal was applied so as to move the mobile 200 by 1 μm to 20 μm for each step repeated thirty times. As described above, the pulse wave power applied to the motor 100 is a signal obtained by combining the signal generated by the external controller with the position information of the mobile 200 fed back from the position sensor 800.

As seen in FIG. 9, the actual displacement value of the mobile 200 increases substantially linearly in accordance with the application of the target displacement input signal for displacing the mobile 200 by 1 μm to 20 μm for each step. That is, according to the embodiment, it is possible to move the mobile 200 with the high positioning ability of 1 μm due to the high resolution of the micro manipulator and the feedback control by the position sensor. In addition, since the mobile 200 is precisely moved due to the linear relationship between the input value and the output value, it is possible to accurately move the electrode to a desired position.

As described above, the position information of the mobile 200 is measured in real time by the position sensor 800, and the position information is fed back to be combined with the signal for operating the motor 100 so as to create a control signal for accurately controlling the motor 100. When the created control signal is applied to the motor, it is possible to precisely control the mobile 200 so that the movement displacement of the mobile 200 is substantially equal to the target value. That is, according to the disclosure, it is possible to very precisely control the operation of the micro manipulator 10 by means of the excellent resolution of the piezo motor and the feedback control of the position sensor.

In other words, the micro manipulator 10 according to the embodiment is capable of moving the mobile 200 with high resolution and of positioning the mobile 200 to an accurate position by correcting an error generated during the operation thereof through the feedback control of the position information of the mobile 200. As a result, it is possible to very precisely and accurately move the electrode connected to the mobile 200. That is, the function of the micro manipulator according to the disclosure is more excellent than that of the known manual micro manipulator having the positional precision and resolution of 10 to 20 μm. Accordingly, since it is possible to more precisely locate the electrode at a desired position, it is possible to improve the possibility of detecting the neuron cell at a desired position.

Figure 10:
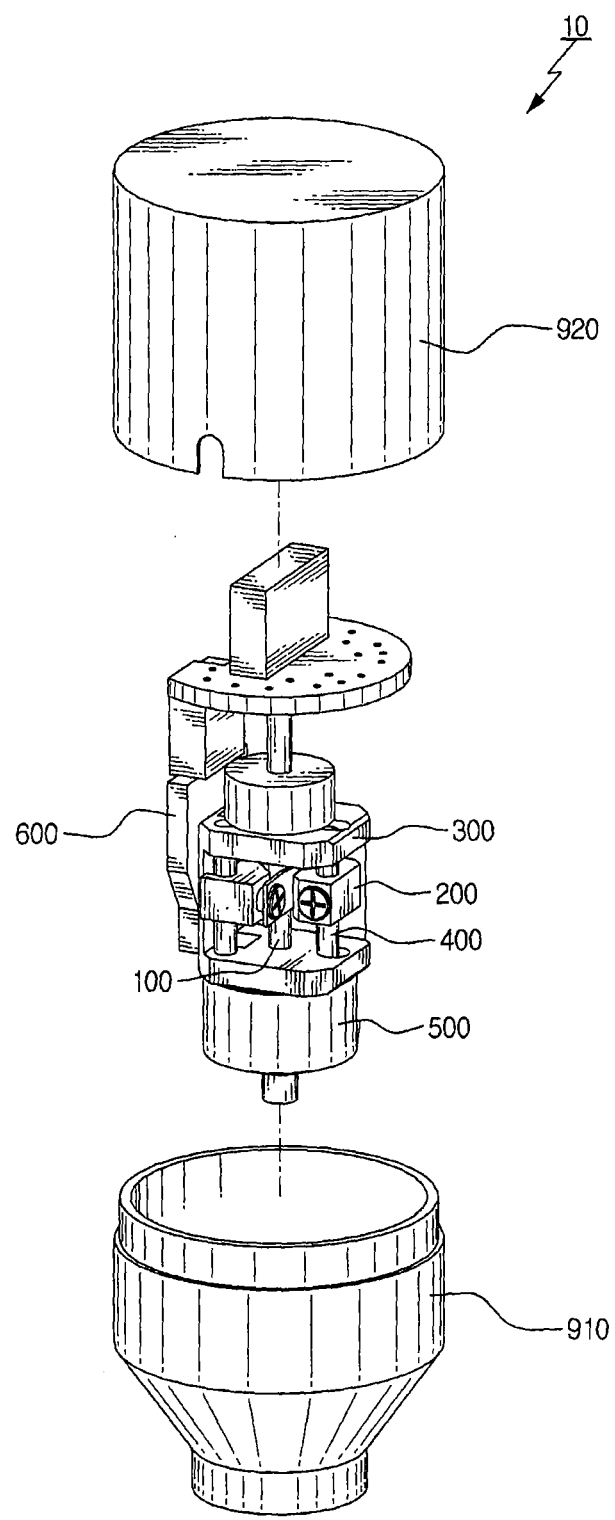
FIG. 10 is a perspective view showing a separated state of the micro manipulator 10 according to still another embodiment of the disclosure.

FIG. 10 is a perspective view showing a separated state of the micro manipulator 10 according to still another embodiment of the disclosure.

According to the embodiment, outer covers 910 and 920 are provided so as to support the motor 100, the mobile 200, and other constituents therein in a fixed state. As shown in FIG. 10, in the embodiment, the outer covers 910 and 920 include a lower cover 910 and an upper cover 920, and the upper cover 920 is separable from the lower cover 910. As shown in FIG. 10, a guide member 500 is coupled to the inside of the lower cover 910 so that the devices constituting the micro manipulator 10 are located inside the lower cover 910.

Figure 11:
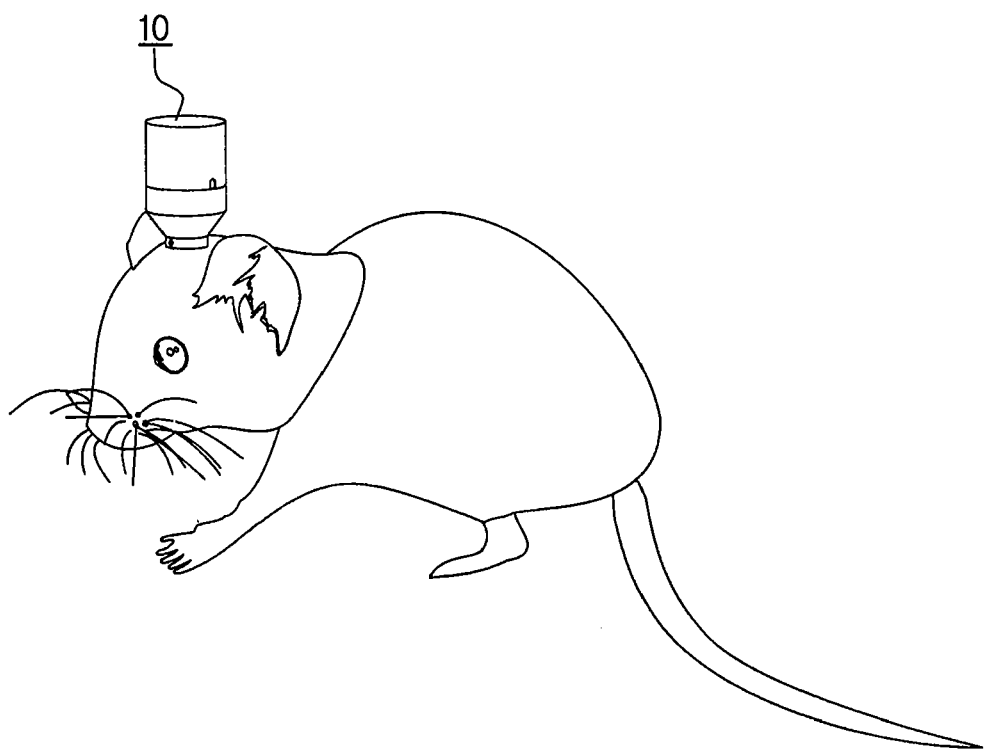
FIGS. 11 and 12 are state diagrams showing a usage state of the micro manipulator 10 according to the embodiment in FIG. 10.
Figure 12:

FIGS. 11 and 12 are state diagrams showing a usage state of the micro manipulator 10 according to the embodiment in FIG. 10.

As shown in FIG. 11, the electrode extending from the micro manipulator is inserted through a head of a subject mouse, and the outer surface of the lower cover 910 of the micro manipulator 10 is attached and fixed to the head of the mouse by using adhesive such as dental cement. As shown in FIG. 12, when detecting the brain neural signal using the micro manipulator 10, the upper cover 920 is removed, and a wire is connected to the signal transmitting device or the like.

By means of the lower cover 910, it is possible to prevent the devices located inside the lower cover 910 from being broken due to the exposure of the devices to the adhesive. Also, by means of the upper and lower covers 910 and 920, it is possible to protect the internal devices from external impact.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

What is claimed is:

1. A micro manipulator comprising:
   a motor which includes a shaft and a single vibration portion;
   a mobile which is coupled to the shaft as to encompass and contact at least a portion of an outer surface of the shaft and is movable along the shaft in a longitudinal direction of the shaft; and
   a frame which supports the motor,
   wherein an electrode is connected to the mobile in a direction parallel to a longitudinal direction of the shaft,
   wherein the shaft is formed in a direction perpendicular to the vibration portion,
   wherein the vibration portion is mechanically curved in a positive direction that is parallel to the longitudinal direction of the shaft by application of power thereto, and wherein the vibration portion is mechanically curved in a negative direction that is parallel to the longitudinal direction of the shaft by removal of the power thereto,
   wherein when the vibration portion is curved in a positive direction by the application of power thereto, the mobile moves in the positive direction together with the shaft due to a frictional force between the shaft and the mobile, wherein when the vibration portion is curved in a negative direction by removal of the power thereto, the mobile remains at the position reached during the application of power to the vibration portion due to inertia force of the weight of the mobile while the shaft moves in a negative direction, so that the mobile moves linearly in a positive longitudinal direction of the shaft and the electrode connected to the mobile moves linearly by linear movement of the mobile.

2. The micro manipulator according to claim 1, wherein the vibration portion includes a deforming plate which extends and contracts upon applying a power thereto and an elastic plate which is attached to the deforming plate, and wherein the shaft is fixed to the deforming plate or the elastic plate and is formed in a direction perpendicular to the elastic plate.

3. The micro manipulator according to claim 1, further comprising:
an electrode holder which is fixed to the mobile and is formed in a direction parallel to the longitudinal direction of the shaft, wherein the electrode is mounted to the inside of the electrode holder so as to be connected to the mobile.

4. The micro manipulator according to claim 3, wherein the electrode holder is separable from the mobile.

5. The micro manipulator according to claim 1, wherein the shaft perforates the center of the frame.

6. The micro manipulator according to claim 5, further comprising:
a funnel-shaped guide member, wherein the guide member is coupled to the center of a lower end of the frame so that an end of the electrode extends along an axis of the shaft.

7. The micro manipulator according to claim 1, further comprising:
a position sensor which measures a displacement of the mobile, wherein the position sensor includes a permanent magnet and a magnetic sensor, and wherein the permanent magnet is fixed to the mobile.

8. The micro manipulator according to claim 7, further comprising:
a position signal transmitting device which is fixed to the frame, wherein the position signal transmitting device transmits information relating to displacement of the mobile measured by the position sensor to an external controller.

9. The micro manipulator according to claim 1, further comprising:
a control signal transmitting device which is fixed to the frame, wherein the control signal transmitting device transmits a motor control signal generated by an external controller to the motor so as to drive the motor.

10. The micro manipulator according to claim 1, further comprising:
an outer cover which supports the motor, the mobile, and the frame therein in a fixed state.

11. The micro manipulator according to claim 10, wherein the outer cover includes an upper cover and a lower cover, and wherein the upper cover is separable from the lower cover.

12. The micro manipulator according to claim 1, further comprising:
a plate spring which is coupled to the mobile, wherein the plate spring is located at a connection portion between the shaft and the mobile so as to apply frictional force between the shaft and the mobile.

\* \* \* \* \*